United States Patent [19]

Svensson

[11] Plant 5,247

[45] Jun. 19, 1984

[54] ROSE PLANT—SCANDINAVIAN

[75] Inventor: Erik Svensson, Kavlinge, Sweden

[73] Assignee: Jackson & Perkins Company, Medford, Oreg.

[21] Appl. No.: 434,116

[22] Filed: Oct. 13, 1982

[51] Int. Cl.[3] ..... A01H 5/00

[52] U.S. Cl. ..... Plt./28

[58] Field of Search ..... Plt./28

*Primary Examiner*—Robert E. Bagwill

*Attorney, Agent, or Firm*—Klarquist, Sparkman, Campbell, Leigh & Whinston

[57] ABSTRACT

This novel rose variety is a mutation of Mercedes and differs therefrom in its bud and blossom colors and occasional white streaks in the blossom petals.

1 Drawing Figure

DETAILED DESCRIPTION OF INVENTION

Figure 1:
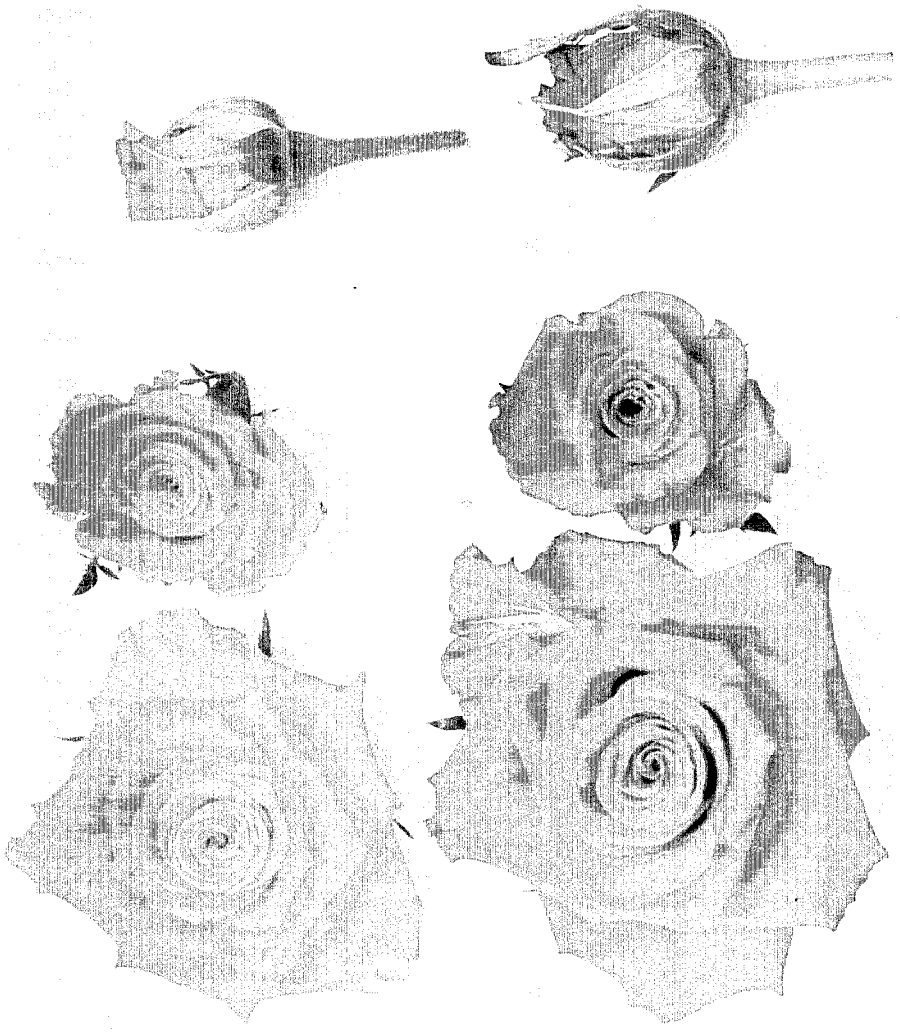

The present invention relates to a new and distinct variety of rose plant of the floribunda class, which was discovered by me as a cultivated sport of the floribunda rose Mercedes (U.S. Plant Pat. No. 3,724), on a plant grown in Sweden.

On the Mercedes rose bush, I discovered that flowers on one of the branches were distinctly different from a normal Mercedes, in both the tight bud and open flower. Propagation of the budding eyes of this one stem proved that this sport came through in successive propagations.

This new cultivar is substantially identical in all respects to its parent, except for the difference in bud and blossom color noted above.

The attached drawing shows the bud and blossom stages of the new cultivar (879) and its parent, Mercedes.

As observed at Irvine, Calif., the new rose variety had a color in tight bud and open blossom in accordance with Munsell's Book of Color of near 5.0 R 3/10. The blossom petals occasionally possess a white streak, a characteristic also present in other sports of Mercedes.

Being substantially identical to the parent variety except for the aforementioned distinctions, reference is made to U.S. Plant Pat. No. 3,724 for further description of this variety.

I claim:

1. A new and distinct variety of rose plant of the floribunda class, substantially as herein shown and described, characterized particularly as to novelty by the described bud and bloom color set forth above on a plant otherwise identical to the variety Mercedes.

* * * * *

MERCEDES